United States Patent [19]

McDonald

[11] 4,103,548

[45] Aug. 1, 1978

[54] WHEEL-WEAR MONITOR

[76] Inventor: Frank W. McDonald, 4420 Choctaw Circle, SE., Huntsville, Ala. 35801

[21] Appl. No.: 774,918

[22] Filed: Mar. 7, 1977

[51] Int. Cl.² .......................................... G01M 17/00
[52] U.S. Cl. .................................................... 73/146
[58] Field of Search ............ 73/146; 246/247, 169 R; 209/1

[56] References Cited

U.S. PATENT DOCUMENTS 2,408,553  10/1946  Gieskieng et al. ............... 246/169 R

OTHER PUBLICATIONS

"Bad Wheels Spotted in Motion", Dec. 16, 1963, Railroad Age, pp. 23 and 30.

*Primary Examiner*—Donald O. Woodiel

[57] ABSTRACT

The disclosure described herein is a Wheel-wear Monitor that identifies wheels on railroad cars which have so worn that wheel flanges, with additional wear, will contact the rail frogs. The device consists of a set of contacts which are actuated by the flange of a worn wheel, an air-pellet gun triggered by said flange, pellets containing paint, a pellet gun control unit, automated reloading accessories, and a load cell sensor.

2 Claims, 16 Drawing Figures

WHEEL-WEAR MONITOR

The Wheel-wear Monitor detects a worn wheel when the rail-mounted contacts are depressed by wheel flanges which have reached excessive length due to wear of the wheel's bearing surface. Sequential pulses from the momentary closure of a series of contact switches are used by a control unit to properly time the firing and reload sequences of an air pellet gun. The air pellet gun propels a paint-filled pellet into the face of a worn wheel. The mark can be utilized by inspectors to identify worn wheels, and on verification by the inspector, the unit can be scheduled for shop maintenance. Indirect measurement of the interval between contact switch activations and an under-rail-load sensor which responds to the weight of a passing freight car used to deactivate the air pellet gun against tampering. Although resources are not discussed further in this disclosure, sources of electrical power and compressed air are required at the site to operate the apparatus.

Illustrations which describe the disclosure are contained in FIGS. 1 through 16.

Figure 1:
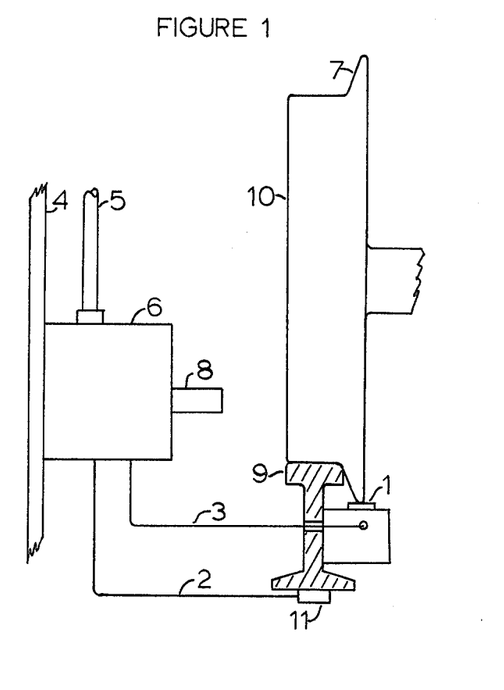
FIG. 1 illustrates the relative locations of components of the track-side apparatus.

The intent of FIG. 1 is to illustrate the physical relationship of various components of the monitoring system to the track rail 9 and truck wheel 10. The wheel flange 7 of a worn wheel has been lengthened due to wheel wear and requires turning down. The excessive flange length depresses the contact switch 1 sufficiently to cause a momentary circuit closure. The circuit closure results in transmission of a pulse over cable 3 to the gun control unit located within the pellet gun and control unit enclosure 6. The pellet gun and control unit are mounted on a support 4 at track side with the pellet gun barrel 8 properly aligned to hit the face of a passing wheel. A load cell sensor 11, mounted beneath the track rail 9, sends a signal over cable 2, indicating that the track is in use, to the the gun control unit. The air supply line 5 is a tubing connection to a source of high-pressure air which is used in operation of the pellet gun reload accessories and in propelling the paint pellet.

Figure 2:
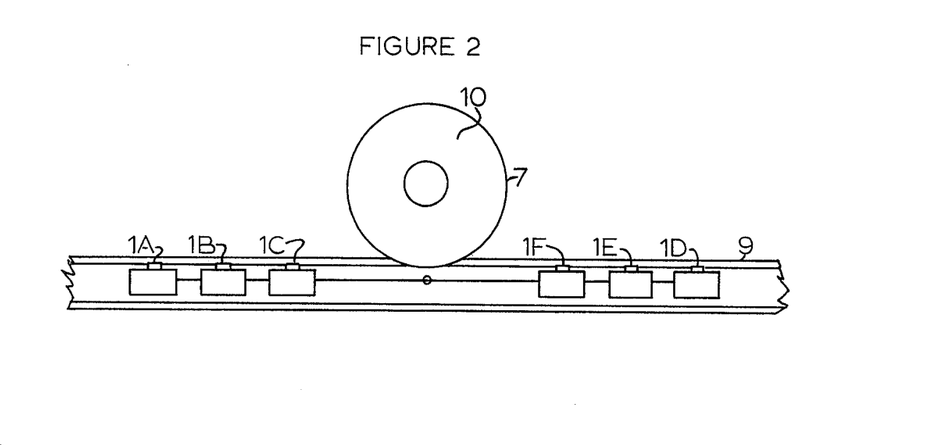
FIG. 2 illustrates the distribution of a plurality of contacts, as attached to the track rail.

FIG. 2 illustrates the multiple contacts 1A, 1B, and 1C arranged in a sequential order relative to passage of a truck wheel 10. As a wheel progresses down the rail 9, the wheel flange 7 depresses the contacts 1A, 1B, and 1C in sequence. An equal distance between contacts is fundamental to the proper operation of the monitor. The time required for the wheel to negotiate the distance between contacts is indirectly measured and utilized to fire the gun at a time which places the paint pellet at the face of the wheel as it passes the pellet gun. Two sets of contacts, with the pellet gun located centrally to the sets, account for traffic in either direction. A second set of contacts comprised of 1D, 1E, and 1F provide the same function for traffic moving in an opposite direction on the track.

Figure 3:
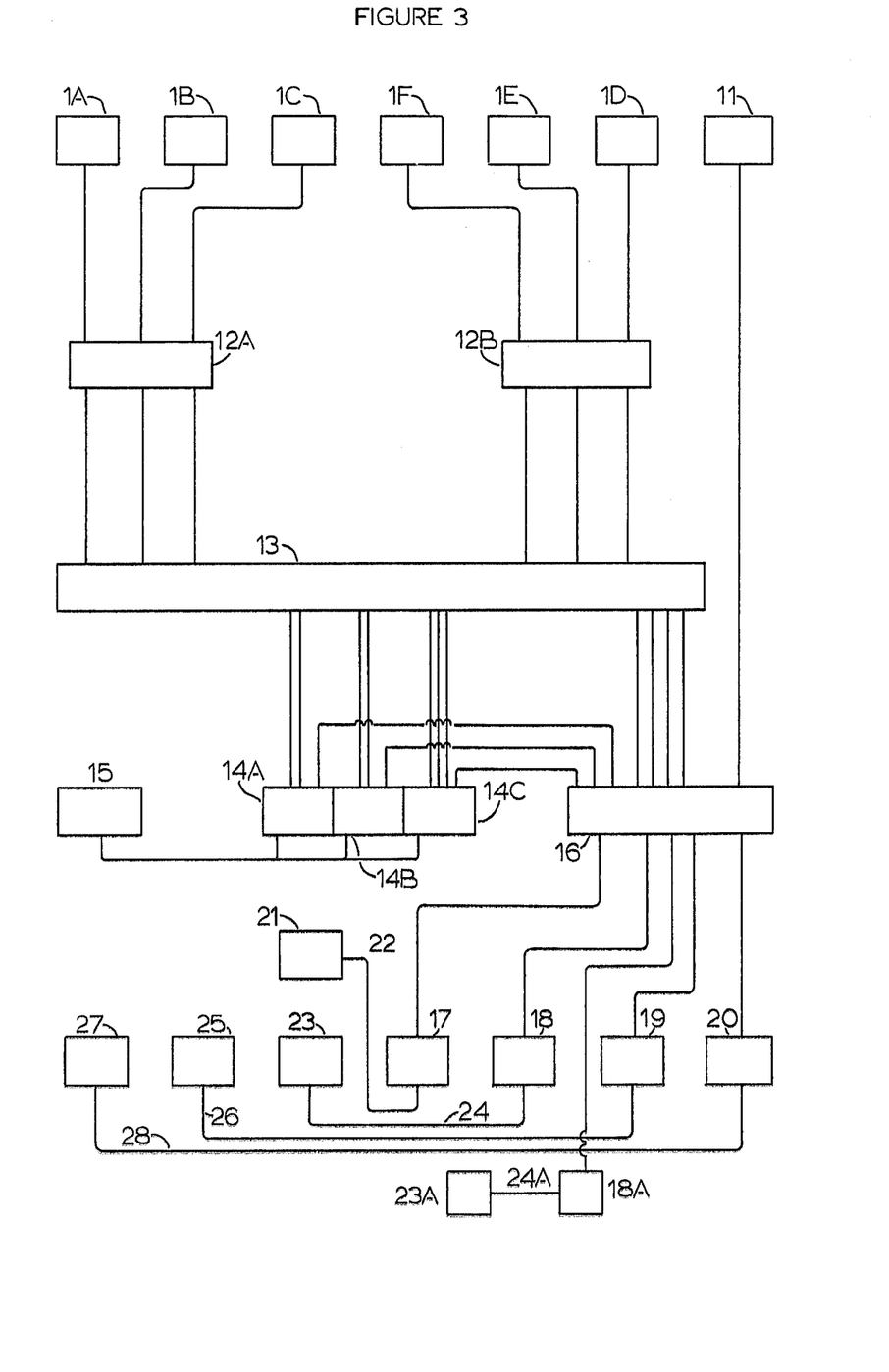
FIG. 3 is a functional block diagram which describes the intraconnection of the components of the control unit. It also describes the functional interconnection of the control unit to the sensing elements and to controlled components of the air pellet gun and reload accessories.

The FIG. 3 block diagram designates the components which comprise the control unit, sensors, and controlled air pellet gun elements and describes the functional intraconnections of the control unit and interconnection between the control unit, sensors, and controlled elements of the air pellet gun.

Pulses from the rail-mounted contacts 1A, 1B, 1C, 1D, 1E, and 1F travel over the interconnections shown between the contacts and the pulse detectors 12A and 12B. (As installed, the interconnected wirings are grouped into a 6-wire pair cable connection represented in FIG. 1 as cable 3. Each wire pair is separated to illustrate the interconnections. The pulse detectors determine the leading edges of the pulses which are generated by the momentary closures of the rail-mounted contacts. The pulse detector unit generates a time-marking signal for each pulse leading edge detected. The time-marking signals are transmitted in sequential order to the logic unit 13.

Assuming that the first pulse is generated in contact 1A, sequential timing signals initiated by the closure of contacts 1A, 1B, and 1C and produced by the pulse detector 12A pass through the logic unit 13 and reach the counters 14A, 14B, and 14C respectively. The signal initiated by contact 1A turns on counter 14A, the signal initiated by 1B turns on counter 14B and stops counter 14A, the signal initiated by 1C starts counter 14C and stops counter 14B. When the first signal reaching the logic unit 13 is initiated by 1A, the logic unit opens the circuit between the pulse detector 12B and the counters. If 1D is the first contact depressed, the logic unit blocks signals initiated by 1A, 1B, and 1C from reaching the counters.

During the periods the counters are on, the counters count the number of cycles produced by the oscillator 15. The number of cycles recorded by the counter 14A is proportional to the time required for the wheel flange to travel the linear distance between contacts 1A and 1B; and in a similar manner, the counts in counter 14B represent the time required for transit from contact 1B to contact 1C. The counts in 14A and 14B are transmitted to the logic unit 13 where the number of oscillator cycles to generation of the gun discharge signal are computed. This is accomplished by first multiplying the cycle count in counter 14A by the ratio of the distance between contact 1A and the barrel of the air pellet gun and the distance between contacts 1A and 1B. Next, a number of cycle counts which represent time delays in the actuation of the gun firing mechanism and pellet travel time to wheel range are deducted from the total; and finally, since counter 14C is the free-running counter, the counts accumulated by counters 14A and 14B are deducted. The projected cycle count is set into the comparator 16 and the air pellet gun will be discharged when counter 14C, which is monitored in the comparator 16, reaches this count—as determined by the comparator—and assuming that the comparator has not detected conditions which indicate tampering with the gun.

The comparator 16 generates a signal which is transmitted to power relay one 17. Presence of a signal on the power relay causes the relay to reverse the direction of current flow through the electrically controlled air valve one 21 which causes the air valve to open. Power is fed to the air valve over cable 22. Removal of the comparator signal causes the valve to close.

The logic unit 13 also computes the number of oscillator cycles which occur prior to post firing gun operations. This is accomplished by adding present counts in the logic unit to the cycle count computed for the gun discharge signal generation. The computed cycle counts are set into the comparator 16 and as counter 14C reaches these cycle counts, the comparator accomplishes the following functions:

a. Removes the signal from power relay one 17 which reverses the current flow through air valve one 21 and closes the valve.

b. Applies or removes a signal to power relay two 18 on alternate air pellet gun firings. When a signal is applied to power relay two 18, compressed air is applied through the reversing valve 23 in one direction. Removal of the signal causes the power relay to reverse the current flow through the electrically controlled valve and the compressed air is applied in an opposite direction through the valve. Power is supplied to the reversing valve 23 over cable 24.

c. Applies and removes power each gun-operating cycle to power relay five 18A which operates air valve four 43A and applies and removes the compressed air source for the reversing valve 23. Power is applied over cable 24A.

d. Applies signals momentarily to power relays three 19 or four 20 on alternate gun firings and synchronized to the operation of the reversing valve 23. When a signal is applied to power relay 19, current through air valve two 25 is reversed and the valve opens; removal of the signal from power relay three 19 again reverses the current flow through the electrically controlled air valve three 25 and the valve closes. Power to the air valve is supplied over cable 26. A similar operation is carried out by the power relay four 20 and air valve three 27 pair. Power is supplied to air valve three 27 over cable 28.

e. Stops counter 14C, resets all counters to zero, and closes all pulse-detector curcuits in readiness for the next overlength flange. Output signals from the comparator 16 also reach the logic unit 13 and initiate computation of timing of the next controlled function.

The cycle counts in counters 14A and 14B are also transmitted to the comparator where the two counts are compared for equality; if the difference between the two counts is not less than a preset tolerance, tampering is indicated and the comparator 16 blocks the firing of the air pellet gun. Also, if the signal received at the comparator 16 over cable 2 from the load cell 11 is not sufficient to indicate the presence of a freight car when compared to a reference voltage, the comparator again blocks the discharge of the air pellet gun. Absence of equality of the counts in the counters 14A and 14B and the inadequate load cell output are used as an indication of tampering with the monitoring apparatus. The only purpose of counter 14B is to provide a second technique to guard against tampering with the equipment.

Figure 4:
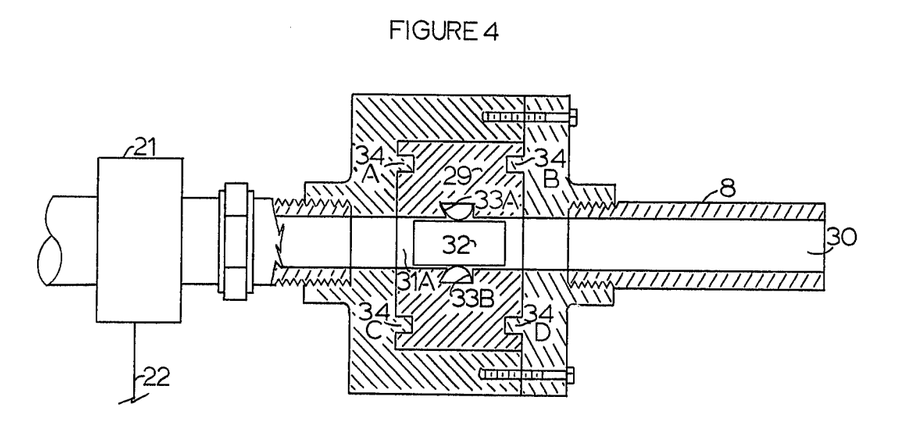
FIG. 4 provides a cross sectional cut-away view of the air pellet gun and also designates the components active in the discharge of the gun.

FIG. 4 is a cross sectional view of the air pellet gun. Also shown is the connection of the air pellet gun into air valve one 21. The air pellet gun contains a shuttle block 29 which has two bore holes which penetrate the block from the back to front sides. The bore holes are of the same diameter as the bore 30 of the air pellet gun. Bore hole 13A is shown aligned with and effectively forming part of the air pellet gun bore. A paint pellet 32 is held in firing position in the shuttle bore, and in turn in the air pellet gun bore. Spring clips 33A and 33B restrain the pellet in the desired position. When a signal from the comparator 16 operates the power relay one 17, as described in FIG. 3, electrical power applied over cable 22 causes the air valve one 21 to open. Compressed air flows into the air pellet gun bore 30 and drives the pellet 32 down the gun bore and into the face of a passing wheel. Reversal of current flow to air valve one, as discussed under the FIG. 3 description, closes air valve one 21 and turns off the compressed air supply, completing the firing of the gun.

Figure 5:
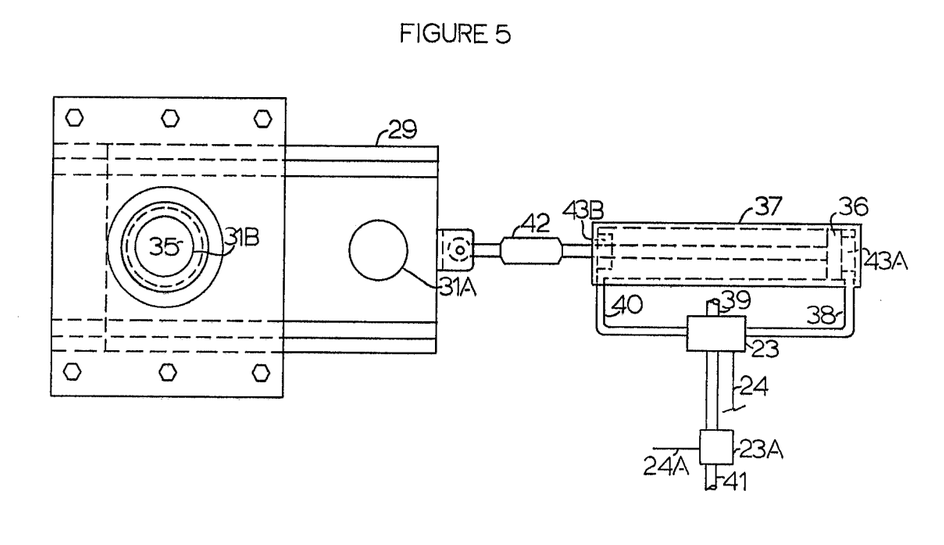
FIG. 5 is a front-elevation view of the air pellet gun which also describes the mechanization which allows a replacement paint pellet to be placed into the gun bore.

Just following closure of the air valve one 21 the shuttle is pulled laterally through the gun, riding on the rectangular tracks 34A, 34B, and 34C, and 34D and into the position shown in FIG. 5.

FIG. 5 illustrates the reload position of the shuttle 29 following firing of a first pellet. FIG. 5 is a frontelevation view of the air pellet gun. Also illustrated is the mechanization of the shuttle 29. Looking into the gun bore 30, a second pellet 35 is shown in firing position in the gun bore, having been carried into this position in the second shuttle bore 31B. Shuttle bore 31A has been carried to the right, out of the gun bore 30 and is in an exposed position from which it can be reloaded.

The shuttle bores were realigned by the piston 36. On close sequence to firing of the air gun, the signal from the comparator 16 to power relay five 18A, which operates air valve five 23A through cable 24A, air valve five 23A applies compressed air to the reversing valve 23. Simultaneously, power to power relay two 18 is either removed or applied, depending on a preselected sequence which is synchronized to move the piston in the proper direction. In keeping with the shuttle motion as currently described, assume that as the gun was fired, the piston 36 is held at the left end of the cylinder 37. Assume that the comparator 16 applies a signal to power relay two 18, of FIG. 3, and reverses the current flow over cable 24 and through the reversing valve 23. Air pressure on the right-hand side of the piston 36 is bled to atmosphere through air line 38 and exhaust port 39 while compressed air is applied to the left side of the piston 36 through air line 40. The piston 36 is driven to the right to the position shown in FIG. 5. This moves the emptied shuttle bore 31A into the reload position shown, and the shuttle bore 31B with pellet 35 into firing position. A signal from the comparator is kept on power relay five 18A just long enough to damp out any bounce the piston 36 may have on reaching the stop at end of cylinder 37. The signal from the comparator is then removed from power relay five 18A, air valve 23A opens, and the compressed air source is removed from the reversing valve 23.

Internal to the cylinder 37, and on each end, are stops 43A and 43B which control the exact distance which the piston 36 can travel. The stops 43A and 43B are magnetic, and perform the dual functions of controlling piston's 36 travel and holding the piston 36 securely in place when the compressed air source is disconnected from the reversing valve 23A.

For reloading of shuttle bore 31B, the piston 36 is driven to the left end of the cylinder 37 through a similar sequence, the only exception being that the comparator 16 removes the signal from power relay 18, reversing current flow through the reversing valve 23. This applies compressed air to the cylinder 37 through air line 38 and exhausts the left end of the cylinder 37 through air line 40 and exhaust port 39. The turnbuckle 42 provides an adjustment of the shuttle's 29 travel, compensating for the lateral mounting position of the cylinder 37. Compressed air source is connected through the pipe 41.

Figure 6:
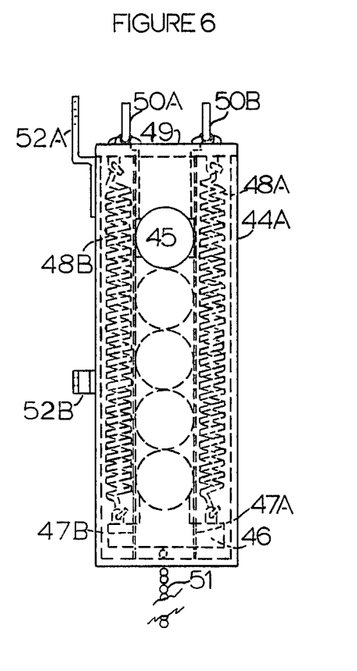
FIG. 6 provides a front-elevation view of a pellet clip, two of which provide the reserve paint pellets for automated multiple reloadings of the air pellet gun.

FIG. 6 is a front-elevation view of a pellet clip 44A. The pellet clip encloses the pellets with the exception that the pellet 45 occupying the topmost position is exposed fore and aft in the clip. Multiple pellets ride on a tray 46 and between guides 47A and 47B. Four springs, one on each corner of the pellet clip, force the tray and pellets upward, replacing the topmost pellet with the next-to-the-top pellet each time a pellet is removed from the clip. Three of the four springs 48A, 48B, and 48C are shown in the views of the pellet clip 44A in FIGS. 6 and 7. The topmost pellet 45 is restrained in the exposed position in the pellet clip by a plug 49 which is form-fit to the top of the pellet. The plug 49 is held in place by pins 50A and 50B. With the pins withdrawn and the plug 49 removed, pellets can be inserted into the pellet clip and the pellet supply replenished. A chain 51 is attached to the bottom of the pellet tray 46 and provides the means to draw the tray 46 to a bottom position. The tray is held down in this position while the pellet clip is reloaded by locking the chain 51 in a key in the bottom plate of the pellet clip. Brackets (52A and 52B) are used to attach the pellet clip to the air pellet gun frame. The pulg 49 is replaced and repinned and the chain 51 is released following the reloading operation.

Figure 7:
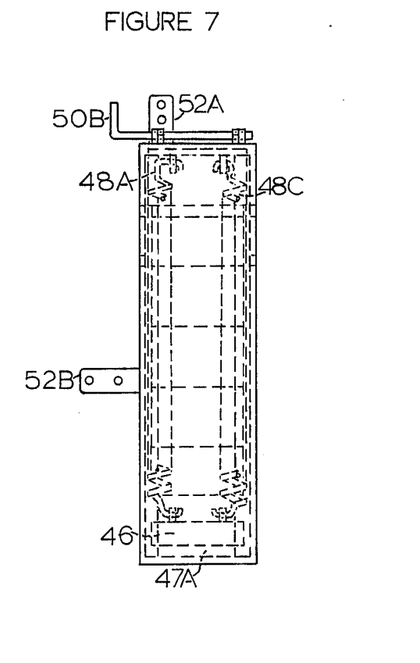
FIG. 7 is a side-elevation view of the pellet clip.

FIG. 7 provides a side-elevation view of the pellet clip of FIG. 6.

Figure 8:
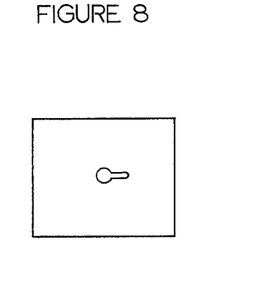
FIG. 8 is a view of the bottom of the pellet clip.

FIG. 8 provides a view of the key on the bottom of the pellet clip.

Figure 9:
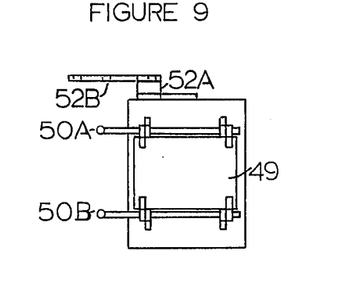
FIG. 9 is a top view of the pellet clip.

FIG. 9 is a top view of the pellet clip. The pins 50A and 50B are inserted through hinge-type cleats. One-half of each hinge is attached to the plug 49 and the other one-half to the top of the pellet clip. Removal of the pins 50A and 50B allows the half attached to the plug 49 to slip past the portion of the hinge attached to the pellet clip.

Figure 10:
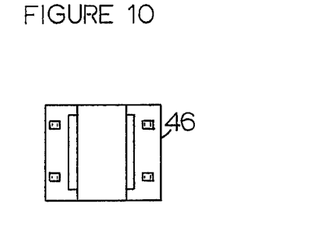
FIG. 10 provides details of the tray on which reserve paint pellets ride within the pellet clips.

FIG. 10 illustrates the tray 46 and the slots 53A and 53B in the tray which ride on the guides 47A and 47B.

Figure 11:
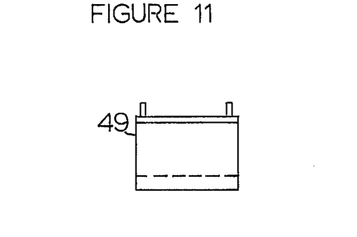
FIG. 11 describes the removable pellet clip component which provides access to the pellet clip for the purpose of replenishing the pellet clip with paint pellets.

FIG. 11 is a side-elevation view of the plug 48.

Figure 12:
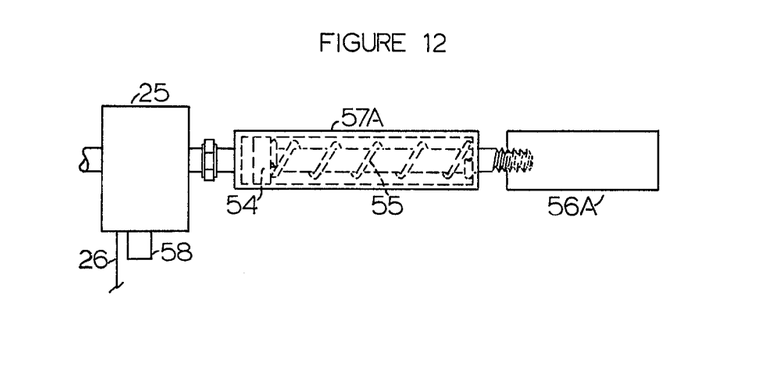
FIG. 12 describes the ram which drives paint pellets from the pellet clips and into the shuttle of the air pellet gun in the reloading process.

FIG. 12 describes the ram used to punch replacement pellets from the pellet clip and into the empty bores of the shuttle 29. When the comparator 16 sends a signal to power relay three 19, the current in the electrically controlled air valve two 25 is reversed and the valve opens, allowing compressed air to force the piston 54 against the spring 55 and driving the ram 56A forward. On removal of the signal by the comparator 16, the current is again reversed; the air valve two 25 closes off the compressed air supply; the spring presses the piston back; and the cylinder 57A is vented to atmosphere through the vent 58. The ram 56A is just slightly smaller than the pellet. When driven forward, it enters the pellet clip; strikes the top pellet 45; and drives it out of the pellet clip and into the waiting bore 31A of the shuttle 29. The ram 56A is of sufficient length and diameter that it places the pellet 45 an adeqate distance into shuttle bore 31A while holding the topmost pellet in the clip down until the ram 56A is snapped back by the spring 55. Clearance between the fore and aft face of the pellets and the front and rear plates of the pellet clip are made sufficiently small to prevent tilting of the pellet in the clip.

Figure 13:
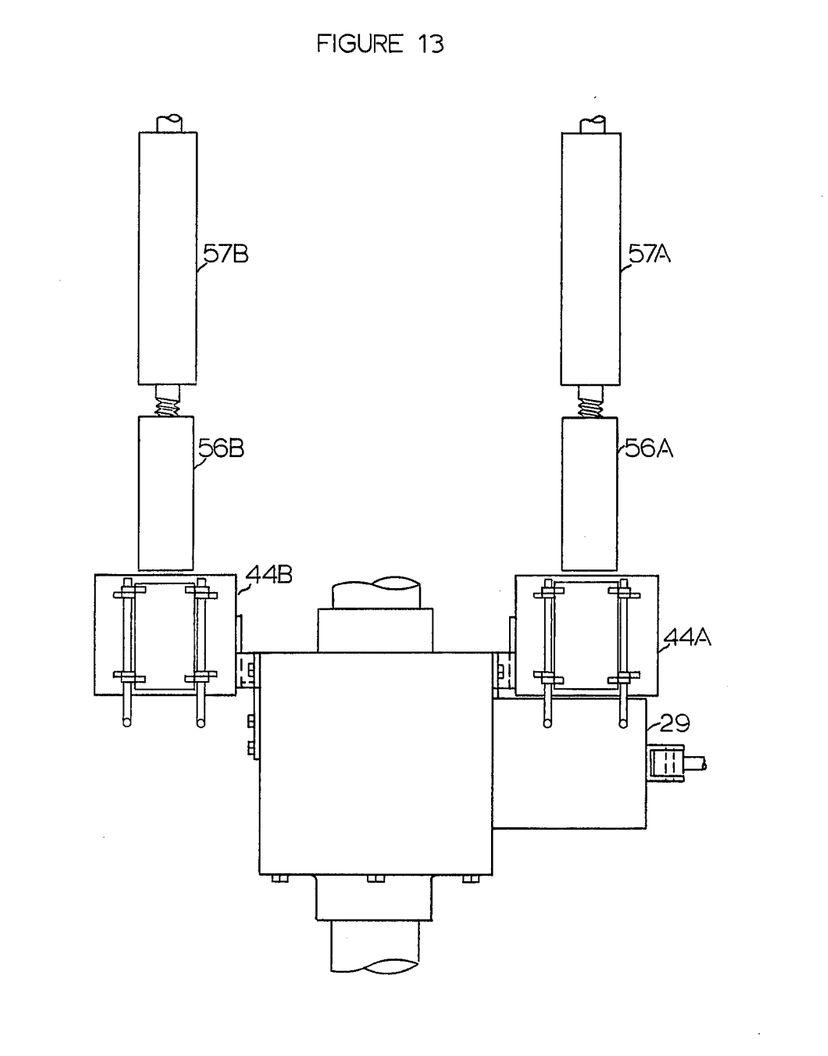
FIG. 13 is a plan view of the air pellet gun with the reload accessories which illustrates the relative positions of these components in an assembled position.

FIG. 13 is a top view of the air pellet gun and reload accessories in their assembled positions. As the shuttle bores 31A and 31B must be loaded from opposite sides of the air pellet gun, the ram 56B and pellet clip 44B are provided to replenish shuttle bore 31B in the same manner as described above for shuttle bore 31A.

The air cylinder 57B is identical to air cylinder 57A. The ram 56B is operated on signal from the comparator 16 on every other air pellet gun firing, and is synchronized with the arrival of an emptied shuttle bore 31B into a reloading position. The power relay four 20 controls air valve three 27 through cable 28, as shown in FIG. 3. Operation of the ram 56B is just as described for ram 56A.

Pellet clips 44A and 44B are identical with the exception of the location of the mounting brackets by which they attach to the air pellet gun frame.

Figure 14:
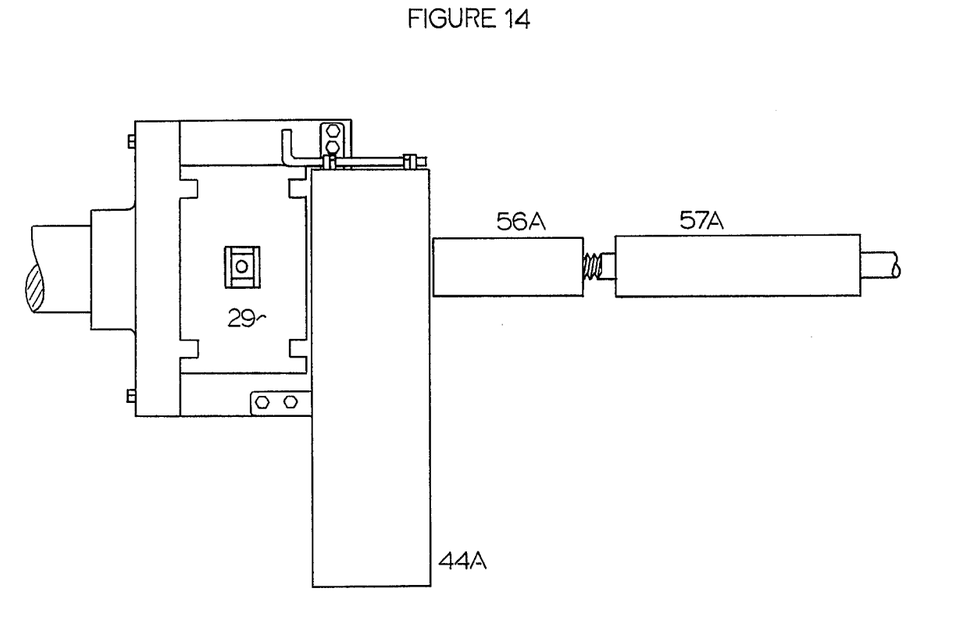
FIG. 14 provides a side-elevation view of the air pellet gun and reload accessories in an assembled condition.

FIG. 14 is a side view of FIG. 13 which provides a little additional information on the positional relationship of the air gun, the shuttle, the pellet clip, and the reload ram within its driving cylinder.

Figure 15:
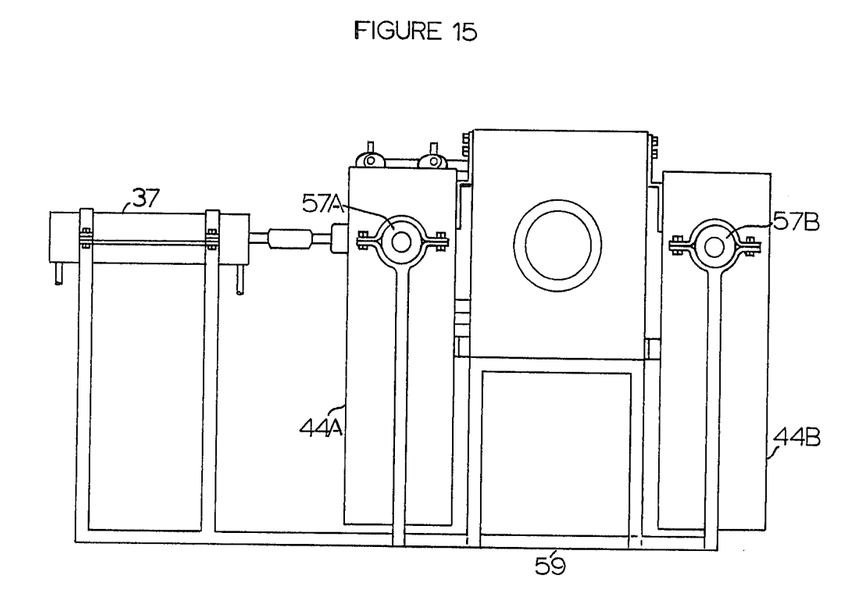
FIG. 15 is a rear-elevation view which describes the mounting framework for the several components which comprise the air pellet gun and reload accessories.
Figure 16:
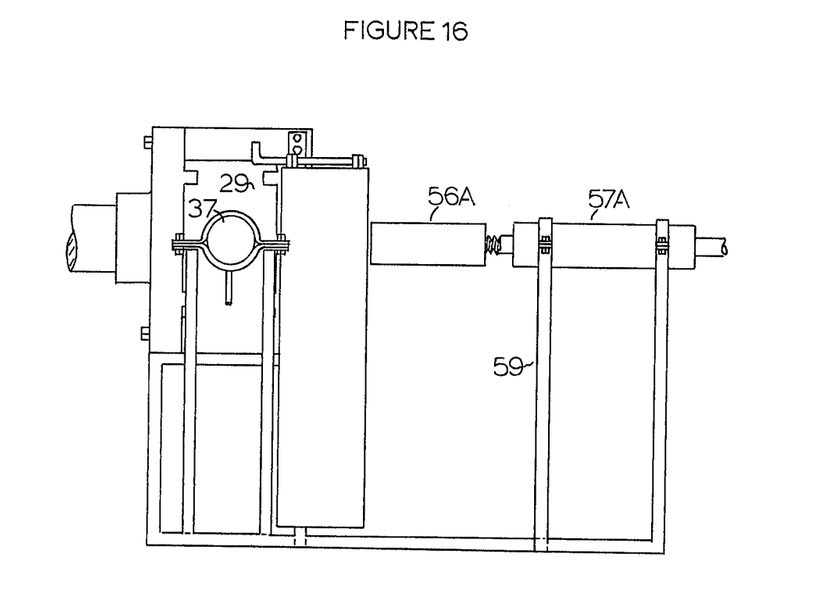
FIG. 16 is a side-elevation view of the gun and reload accessory framework.

FIGS. 15 and 16 are merely intended to show a means of mounting the pellet gun and those reload accessories which must be mounted in fixed relative positions. The air valves are not premounted, as the specific mounting locations are not critical.

FIG. 15 is a rear-elevation view of the air pellet gun showing the mounting of the cylinder 57A, 57B, and 37 mounted in a one-piece welded frame 59. The cylinders are mounted by means of ring clamps; the air pellet gun frame rests directly on the frame 59. As shown, the pellet clips 44A and 44B bold directly to the gun frame.

FIG. 16 provides a side-elevation view of the equipment shown on FIG. 15.

I claim:

1. Apparatus mounted at track side which detects over-length flanges of freight car wheels, predicts wheel position for the purpose of marking, marks the wheel with a pneumatically driven paint pellet, and is comprised of:

a. Multiple rail-mounted contacts, one set for each direction of train travel, so positioned with respect to the rail surface that flanges of worn wheels momentarily actuate the switches, sending pulses to pulse detectors;

b. pulse detectors which receive the input pulses from the rail-mounted contacts and generate a timing marker which passes through the logic unit and actuates counters;

c. a logic unit which is selective between two sets of rail-mounted contacts, as required for direction of travel of the train and which utilize the output of counters in conjunction with constants derived from the installation configuration to compute and transmit to the comparator, timing values required to produce timed signals that discharge an air pellet gun, operate the shuttle in the air pellet gun for the purpose of reloading the gun, operate the reload accessories which reload the gun, cut off counter (14C), and reset all counters to zero in readiness for detection of the next overlength flange;

d. a comparator which (1) compares the outputs of counters (14A and 14B) for equality and monitors the output of an underrail load cell to prevent tampering and (2) compares the output of a free-running counter, (14C) with timing values from the logic unit and on coincidence (3) generates signals which operate pneumatic valves and apply and remove compressed air to and from the air gun discharge chamber, drive the shuttle in the air pellet gun to reload the gun, drive reload rams to reload the shuttle, stop counter (14C), and resets the counters to zero in preparation for the next overlength flange;

e. counters which are activated and deactivated by signals from pulse detectors (14C deactivated by comparator generated signal) and which count cycles of a time base oscillator that are transmitted to the comparator and, in the case of counters 14A and 14B, to the logic unit;

f. reload accessories consisting of refillable spring-loaded clips with paint pellets and electrically controlled pneumatic pistons which punch paint pellets from the clips into bores in the shuttle in the air pellet gun;

g. an oscillator which provides the signal to the counters and provides the time base for predicting an intercept of a paint pellet and a wheel in motion and a means for synchronizing the apparatus operations;

h. a load cell which the comparator monitors to assure the presence of a train on the track, and i. an air-pellet gun which is discharged by an electrically controlled pneumatic valve, on signal from the comparator, and which drives a marking paint pellet into the face of a wheel.

2. The air pellet gun of claim 1 which is discharged by compressed air from an electrically controlled pneumatic valve, incorporates an air piston actuated shuttle which rides on tracks and holds one pellet in immediate firing position in the discharge chamber, and on firing of the first pellet, allows placement of a second pellet in the discharge chamber and the emptied pellet bore in position for automated reloading from pellet clips.

* * * * *